(12) United States Patent
Bonnin et al.

(10) Patent No.: US 11,531,217 B2
(45) Date of Patent: Dec. 20, 2022

(54) METHOD FOR DETERMINING A PARAMETER OF AN OPTICAL EQUIPMENT

(71) Applicant: ESSILOR INTERNATIONAL, Charenton-le-Pont (FR)

(72) Inventors: Thierry Bonnin, Charenton-le-Pont (FR); Pascal Allione, Charenton-le-Pont (FR); Jean Sahler, Charenton-le-Pont (FR); Stéphane Gueu, Charenton-le-Pont (FR); Sébastien Maurice, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 924 days.

(21) Appl. No.: 16/340,808

(22) PCT Filed: Oct. 5, 2017

(86) PCT No.: PCT/EP2017/075424
§ 371 (c)(1),
(2) Date: Apr. 10, 2019

(87) PCT Pub. No.: WO2018/069164
PCT Pub. Date: Apr. 19, 2018

(65) Prior Publication Data
US 2019/0265517 A1    Aug. 29, 2019

(30) Foreign Application Priority Data

Oct. 11, 2016   (EP) ..................................... 16306340

(51) Int. Cl.
*G02C 13/00*   (2006.01)
*A61B 3/11*    (2006.01)
*G02C 7/02*    (2006.01)

(52) U.S. Cl.
CPC ............ *G02C 13/005* (2013.01); *A61B 3/111* (2013.01); *G02C 7/027* (2013.01)

(58) Field of Classification Search
CPC .... G02C 13/005; G02C 7/027; G02C 13/003; G02C 7/14; A61B 3/111
(Continued)

(56) References Cited

U.S. PATENT DOCUMENTS 5,855,074 A   1/1999   Abitbol et al.
6,199,983 B1  3/2001   Kato et al.
(Continued)

FOREIGN PATENT DOCUMENTS

DE   10 2014 015 671 A1   4/2016
EP            1154302 A1   11/2001
(Continued)

OTHER PUBLICATIONS

International Search Report and Written Opinion, dated Dec. 7, 2017, from corresponding PCT application No. PCT/EP2017/075424.
(Continued)

*Primary Examiner* — Stephone B Allen
*Assistant Examiner* — Rahman Abdur
(74) *Attorney, Agent, or Firm* — Nixon & Vanderhye (57) ABSTRACT

Disclosed is a method for determining a parameter of an optical equipment including an optical lens including permanent markings and being mounted in a spectacle frame, including: positioning the optical equipment is before a pattern in a first position; positioning a portable electronic device including an image acquisition module in a second position so as to acquire an image showing together the pattern seen through at least part of the optical lenses of the optical equipment in the first position and at least part of the spectacle frame of the optical equipment in the first position;
(Continued)

detecting the permanent marking on the optical lens using the image acquired by the image acquisition module of the portable electronic device in the second position; and determining at least one parameter of the optical equipment based on the position of the permanent marking.

20 Claims, 3 Drawing Sheets

(58) Field of Classification Search
USPC .............................. 351/159.42, 159.75, 204
See application file for complete search history.

(56) References Cited

U.S. PATENT DOCUMENTS

| | | |
|---|---|---|
| 6,637,880 B1 | 10/2003 | Yamakaji et al. |
| 6,871,955 B2 | 3/2005 | Yamakaji et al. |
| 2007/0121100 A1* | 5/2007 | Divo .................... G02C 13/005 356/124 |
| 2015/0293382 A1* | 10/2015 | Jethmalani ........... G02C 13/003 351/204 |
| 2015/0300912 A1 | 10/2015 | Allione |
| 2017/0035289 A1 | 2/2017 | Boutinon et al. |
| 2017/0336654 A1 | 11/2017 | Seitz et al. |

FOREIGN PATENT DOCUMENTS

| | | | |
|---|---|---|---|
| FR | 3 000 233 B1 | 6/2014 | |
| FR | 3 019 459 A1 | 10/2015 | |
| WO | WO-2015125847 A1 * | 8/2015 | ............. A61B 3/085 |

OTHER PUBLICATIONS

Office Action issued in Chinese Patent Application No. 201780062838.5 dated Nov. 11, 2020.
Communication pursuant to Article 94(3) EPC in European Patent Application No. 17 777 305.8, dated May 20, 2022.

* cited by examiner

METHOD FOR DETERMINING A PARAMETER OF AN OPTICAL EQUIPMENT

FIELD OF THE INVENTION

The invention relates to a method for determining a parameter of an optical equipment, a device for determining at least one parameter of an optical equipment, a method for ordering a new optical equipment and a method for providing a new optical equipment to a person.

BACKGROUND OF THE INVENTION

Usually, a person wishing to have an optical equipment goes to see an eye care practitioner.

The eye care practitioner orders the eyewear equipment at an optical lab by sending an order request to the optical lab. The order request may comprise wearer data, for example the wearer's prescription, fitting data, spectacle frame data, for example the type of spectacle frame the wearer has selected, and lens data, for example the type of optical lens the wearer has selected.

The determination of the wearer's prescription and fitting data may require carrying out complex and time consuming measurements. Such measurements usually require complex and costing material and qualified personnel to be carried out.

Such measurements are usually carried out even when the person's optical needs have not changed. For example, a person that wants to order a new frame with the same optical lenses than with his/her previous spectacles may have to go through the tedious process indicated previously.

The eye care practitioner may use lens mapper and/or lens meter to determine the optical features of the current optical lenses of the optical equipment of the person. However, such devices still require going to the eye care practitioner since there are very expensive and require qualified person to be used. In other words, the person himself may not use such devices to determine the parameters to be included in the order request. Typically, such devices are not available when a person wishes to order a new optical equipment over the internet.

Therefore, there is a need to a method and a device that would allow a person to quickly, easily and at low cost determined optical parameters of his/her current optical equipment.

One object of the present invention is to provide such method.

SUMMARY OF THE INVENTION

To this end, the invention proposes a method for determining a parameter of an optical equipment comprising an optical lens comprising permanent markings and being mounted in a spectacle frame, the method comprising:
  an optical equipment positioning step, during which the optical equipment is positioned before a pattern in a first position,
  a portable electronic device positioning step, during which a portable electronic device comprising an image acquisition module is positioned in a second position so as to acquire an image showing together the pattern seen through at least part of the optical lenses of the optical equipment in the first position and at least part of the spectacle frame of the optical equipment in the first position,
  a permanent marking detection step, during which the at least one permanent marking on the optical lens is detected by using the image acquired by the image acquisition module of the portable electronic device in the second position,
  a parameter determining step during which at least one parameter of the optical equipment is determined based on the position of the permanent marking.

Advantageously, the method of the invention allows a person to determine parameters, for example optical parameters, of his/her current optical equipment by simply using a portable electronic device, such as a smartphone, a tablet computer or a laptop.

According to further embodiments which can be considered alone or in combination:
  the method further comprises prior to the parameter determining step a scaling step during which the scale of the image of the optical equipment is determined based on the standard distance of two permanent alignment markings on the same optical lens and/or by using a known size element positioned in the average plane of the optical equipment; and/or
  the at least one parameter of the optical equipment is selected in the list consisting of the pupillary distance, the half-pupillary distance, height parameters, the far distance centering point, the addition of the progressive lens, the lens manufacturer; and/or
  during the parameter determining step the position of the distance visual point relative to a reference point of the spectacle frame is determined; and/or
  the reference point of the spectacle frame is a reference point of the nose pad of the spectacle frame; and/or
  the pattern is periodical; and/or
  the pattern is static; and/or
  the pattern is dynamic; and/or
  the position of the far vision reference point of the optical lens is determined during the parameter determining step; and/or
  during the parameter determining step at least one optical parameter of the optical lens is determined based on the image of the pattern seen through at least part of the optical lens of the optical equipment in the first position; and/or
  the method further comprises a position determining step during which the distance and the relative orientation between the image acquisition module and the optical equipment are determined; and/or
  the distance and relative orientation between the image acquisition module and the optical equipment are determined using at least measuring means of the portable electronic device; and/or
  the optical equipment comprises two optical lenses mounted in a spectacle frame and the method further comprises an interpupillary distance determining step during which the interpupillary distance of the user for which the optical equipment is intended is determined based on the position of the permanent marking; and/or
  the optical lens is a progressive ophthalmic lens.

The method further relates to an ordering method for ordering a new optical equipment for a user of a first optical equipment, the ordering method comprises:
  a parameter determining step during which at least one parameter of the first optical equipment of the user is determined by a method according to the invention, and
  an ordering step during which an order request for a new optical equipment is sent to a distant entity, the order request comprising the value of the at least one parameter and new optical equipment identification data.

The invention further relates to an optical equipment providing method for providing a new optical equipment for a user of a first optical equipment, the method comprising:
- an order receiving step during which an order request generated by an ordering method of the invention is received,
- a new optical equipment parameter determining step during which at least one parameter of the new optical equipment of the user is determined based on the value of the parameter of the first optical equipment determined during the parameter determining step,
- an optical equipment providing step during which a new optical equipment is provided to the user based on the value of the at least one parameter determined during the new optical equipment parameter determining step.

According to an embodiment of the optical equipment providing method according to the invention may, during the new optical equipment parameter determining step at least one parameter of the new optical equipment of the user is determined as substantially the same as the parameter determined during the parameter determining step.

The invention also relates to a device for determining at least a parameter of an optical equipment comprising an optical lens comprising permanent markings and being mounted in a spectacle frame, the device comprising:
- a receiving element configured to physically receive the optical equipment in at least a first predetermined position,
- an acquisition receiving element configured to physically receive a portable electronic device having an image acquisition module in at least a second predetermined position relative to the optical equipment received by the receiving element so as to acquire an image of a pattern seen through at least part of the optical lenses of the optical equipment received by the receiving element,
- a permanent marking detection element configured to process the image of the pattern seen through at least part of the optical lenses of the optical equipment to detect at least one permanent marking on the optical lens, and
- a parameter determining module configured to determine at least one parameter of the optical equipment is determined based on the position of the permanent marking.

The invention further relates a method for ordering a new optical equipment for a user of a first optical equipment, the method comprising:
- an optical equipment positioning step, during which the first optical equipment comprising a first pair of optical lenses having permanent markings mounted on a first spectacle frame is positioned in a first position,
- a portable electronic device positioning step, during which a portable electronic device comprising an image acquisition module is positioned in a second position so as to acquire an image of a pattern seen through at least part of the optical lenses of the first optical equipment in the first position,
- an acquisition step during which at least one image of the pattern seen through at least part of the optical lenses of the first optical equipment is acquired,
- an ordering step during which an order request for a new optical equipment is sent to a distant entity, the order request comprising the at least one image acquired by the portable electronic device and new optical equipment identification data.

The method may further comprise:
- a permanent marking detection step, during which the at least one permanent marking on the optical lens is detected by using the image acquired by the image acquisition module of the portable electronic device in the second position, and
- a parameter determining step during which at least one parameter of the optical equipment is determined based on the position of the permanent marking.

The invention also relates to a method for providing optical equipment for a person, the method comprising:
- an order receiving step during which an order request generated by a method according to the invention and comprising at least an image of a predetermined element seen through at least part of the optical lenses of the first optical equipment of the person is received,
- a parameter determining step during which at least one optical parameter of the optical equipment is determined based on the at least one received image,
- an optical equipment providing step during which a new optical equipment is provided to the person based on the at least one optical parameter determined during the parameter determining step.

The invention further relates to a computer program product comprising one or more stored sequences of instructions that are accessible to a processor and which, when executed by the processor, causes the processor to carry out at least the steps of the method according to the invention.

The invention also relates to a computer-readable storage medium having a program recorded thereon; where the program makes the computer execute at least the steps of the method of the invention.

The invention further relates to a device comprising a processor adapted to store one or more sequence of instructions and to carry out at least steps of the method according to the invention.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Elements in the figures are illustrated for simplicity and clarity and have not necessarily been drawn to scale. For example, the dimensions of some of the elements in the figure may be exaggerated relative to other elements to help improve the understanding of the embodiments of the present invention.

The invention relates to a method for determining a parameter of an optical equipment comprising an optical lens comprising permanent markings and being mounted in a spectacle frame.

An ophthalmic lens is usually designed to be mounted in a spectacle frame and positioned before the eye of a wearer, according to the prescription of the wearer. The prescription notably includes, in case of a progressive lens, addition as well as power in far and near vision and if needed prism.

To ensure installation and positioning of the ophthalmic lens in accordance with the needs of a wearer, any progressive ophthalmic lens has specific permanent markings. In particular, permanent markings, such as micro engravings, for example micro circles, are set up on one side of the lens.

These permanent markings are intended to allow an identification of all points of interest from a template associated with the lens. Permanent markings are required under ISO standard ISO10322-2 and 8980-2. Additional markings whether permanent or not, may be provided by the lens manufacturer.

For each type of lens there is a template which is provided by the manufacturer of the lens. Such templates may be render available and user to identify the set of points of interest on an ophthalmic lens.

Figure 5:
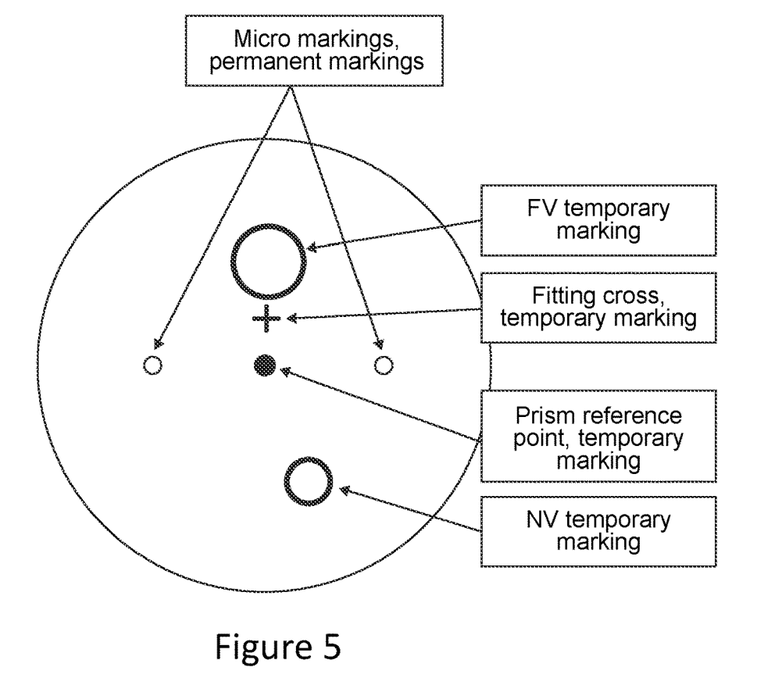
FIG. 5 shows a lens bearing examples of markings applied by the lens manufacturer.

Progressive lenses comprise micro-markings that have been made mandatory by the harmonized standard ISO 8980-2. Temporary markings may also be applied on the surface of the lens, indicating diopter measurement positions (sometimes referred to as control points) on the lens, such as for far vision and for near vision, a prism reference point and a fitting cross for instance, as represented schematically in FIG. 5.

It should be understood that what is referred to herein by the terms far vision control point and near vision control point can be any one of the points included in the orthogonal projection on the first surface of the lens, of respectively the FV and NV temporary markings provided by the lens manufacturer. If the temporary markings are absent or have been erased, it is always possible for a skilled person to position such control points on the lens by using a mounting chart and the permanent micro-markings.

The micro-markings also make it possible to define referential for both surfaces of the lens.

The points of interest that a may be identified using the permanent marking and the template include:
  the prism reference point,
  the fitting cross,
  the far vision control point to control the far vision prescription before shipping the ophthalmic lens fitted to the wearer,
  the near vision control point to control the near vision prescription before shipping the ophthalmic lens fitted to the wearer.

Figure 1:
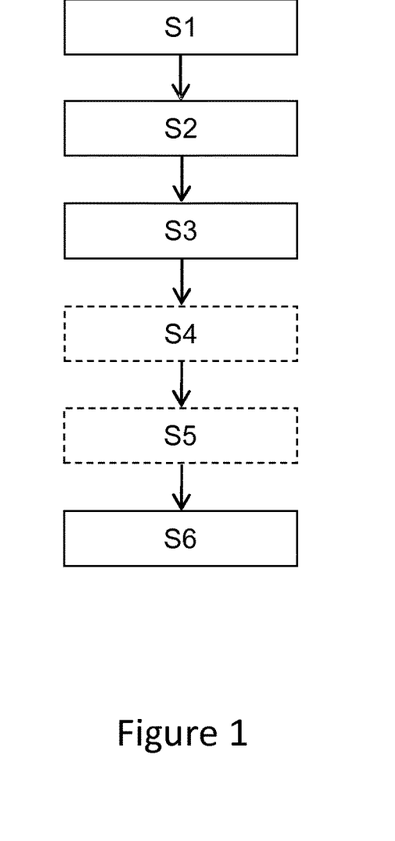
FIG. 1 is a flow chart representing a method for determining a parameter of an optical equipment according to the invention.

As illustrated on FIG. 1, the method for determining a parameter of an optical equipment according to the invention comprises at least:
  an optical equipment positioning step S1,
  a portable electronic device positioning step S2,
  a permanent marking detection step S3, and
  a parameter determining step S6.

During the optical equipment positioning step S1, an optical equipment comprising at least an optical lens comprising permanent markings and being mounted on a spectacle frame is positioned before a pattern in a first position.

The pattern is preferably periodical and may be static or dynamic. An example of pattern may be a grid, equally spaced dots, letters from a book or a newspaper, symbols etc . . . positioned at a given distance of the optical equipment.

The pattern may be displayed using a display device, such as a TV or computer screen or a smart phone display. The pattern may also be a paper pattern, for example a pattern printed previously.

Preferably, the features of the pattern have a width of at least three times the resolution of the acquisition module in order to have an accurate measurement of the position of the different features.

The pattern has preferably high contrast, for instance black and white, or white and green gratings.

The physical size of the pattern may be known, and this size can be known from a size value input from the user, from a measurement using a photo of both the pattern and a known size element, such as a credit card, or from normalized value of the pattern, for example the normalized size of a sheet of paper having 5 mm square grid used as a pattern.

Figure 4:
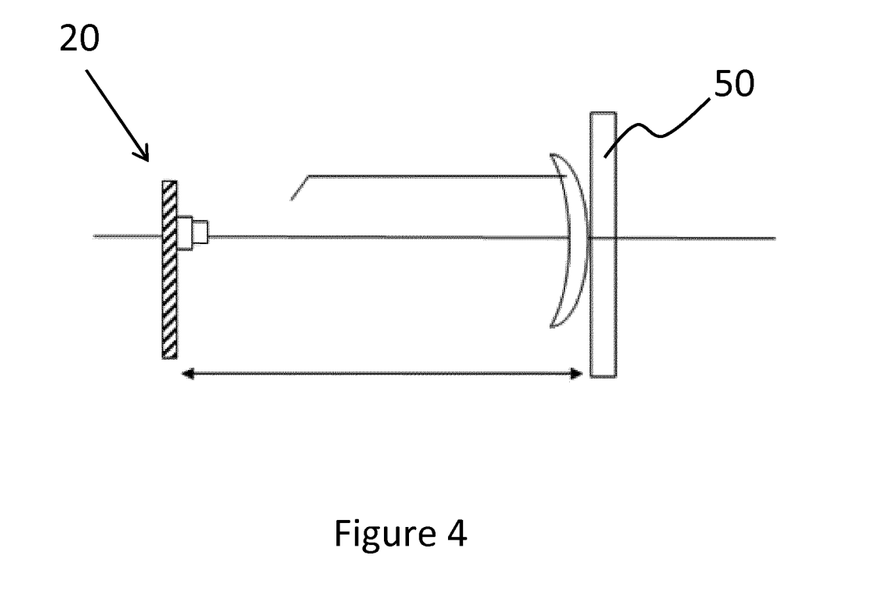

The display of the pattern and the acquisition of the images can be performed by only one device, for example, a smartphone or a laptop, by using a mirror 50 as illustrated on FIG. 4.

During the portable electronic device positioning step S2, a portable electronic device comprising at least an image acquisition module, for example a camera, is positioned in a second position. The second position may be determined and/or known relatively to the first position in which the optical equipment is positioned during step S1.

The optical equipment and the portable electronic device are positioned so as to allow acquiring by the image acquisition module of the portable electronic device, an image of the pattern seen through at least part of the optical lens of the optical equipment in the first position.

According to some embodiment of the invention a specific zone of the optical lenses may be of interest, such as the optical center for a single vision lens, or the far and/or near vision zone for a multifocal lens. In such case an image of the pattern seen through such specific zones of the optical lenses may be sufficient to determine optical parameters of the optical lenses.

In a preferred embodiment, the optical equipment and the portable electronic device are positioned so as to allow acquiring an image of the pattern seen through all of the optical lenses of the optical equipment in the first position. Advantageously, having an image over all the surface of each optical lenses provide more accurate and precise determination of the optical parameters of the optical lens of the optical equipment.

Figure 2:
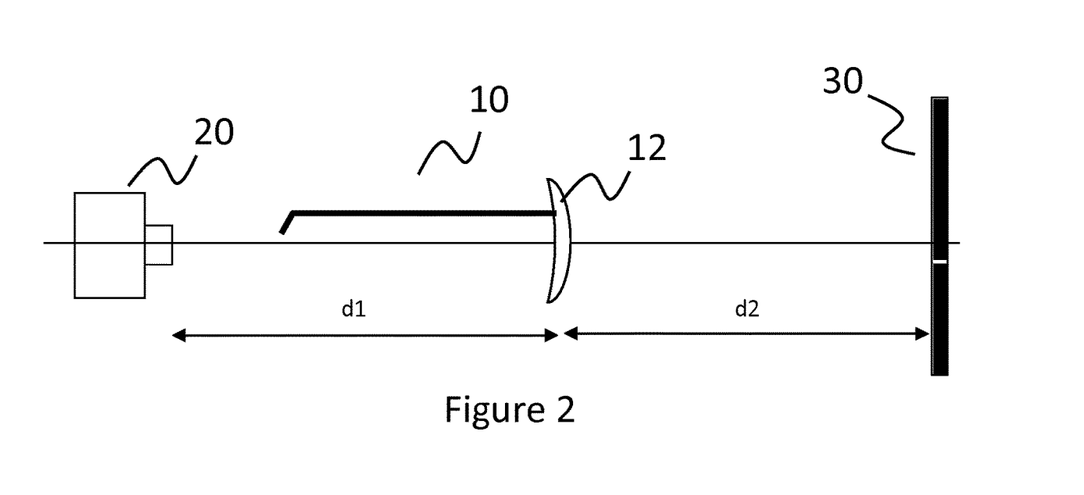
FIG. 2 illustrates the positioning a portable electronic device, an optical equipment and a pattern according to a method of the invention.

FIG. 2 illustrates an example in which a pair of spectacles 10 is positioned between a camera 20 of a portable electronic device at a distance d1 and a pattern 30 at a distance d2.

As illustrated in FIG. 2, the pair of spectacles 10 and the camera 20 are positioned so that an image of at least part of the pattern 30 seen through at least part of the optical lenses 12 of the pair of spectacle can be acquired by the camera 20.

In the sense of the invention, the portable electronic device is any portable electronic device comprising an image acquisition module, such as a camera, CMOS or CDD. For example, the portable electronic device may be a smartphone, a personal digital assistant, or a tablet computer.

The portable electronic device preferably comprises a memory to store executable computer programs and data and a processor to execute the stored computer program. The portable electronic device may further comprise a communication unit to allow the portable electronic device to communicate data with distant device. The communication unit may be configured either for a wire connection or a wireless connection using for example WIFI or Bluetooth® technology.

The wire connection may also by a USB type. The portable electronic device may comprise a memory storing data and the data may be communicated to distant entity using a cable connection.

In order to achieve accurate measurements, it is recommended that during the optical equipment positioning step the frame is not positioned in any manner relative to the image acquisition module. Indeed, poor positioning of the frame may result in significant errors in the measurement of optical parameters of the optical lenses.

Figure 3:
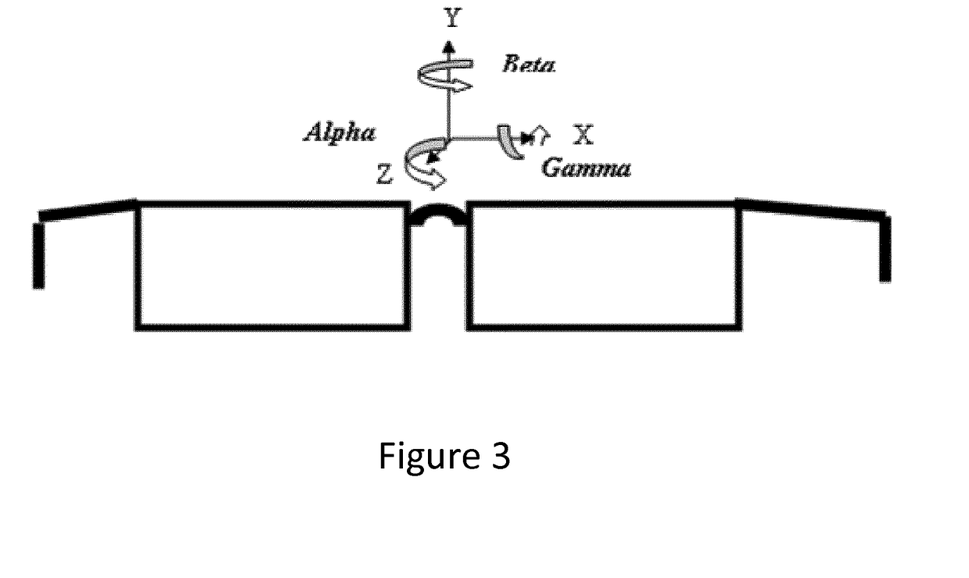
FIG. 3 illustrates the orientation of a spectacle frame, FIG. 4 illustrate an example of device according to the invention.

For example, it is desirable that:
the frame is placed horizontally, adjusting angle Alpha as represented on FIG. 3,
the branches of the spectacle frame are parallel to the optical axis of the acquisition module in a horizontal plane, adjusting angle Beta as represented on FIG. 3,
the branches of the spectacle frame are parallel to the optical axis of the acquisition module in a vertical plane, or a slight angle of about 10° to compensate the pantoscopic angle, adjusting the angle Gamma as represented on FIG. 3.

To assure a correct position of the optical equipment, the portable electronic device may comprise a position help module that provides a feedback to the user on how to position the optical equipment. This is particularly useful when the user needs to hand both the optical equipment and the electronic device, because positioning may be more difficult for the user.

The positioning of the frame (Beta, Gamma) can be achieved via a visual aid on a screen, for example the screen of the portable electronic device to ensure an accurate measurement.

For example, the frame is shot, and the portable electronic device comprises an image processing unit or communicates data with a distant entity comprising the image processing unit. The image processing unit is capable of checking that angle Beta is close to 0 by checking the symmetry of right sides/left of the frame.

If the symmetry is poor, it is indicated on the screen how to orient the spectacle frame or the portable electronic device to correct this.

In a similar manner, it can be checked by image processing that the sides of the frame are parallel to the optical axis of the acquisition module: the image of the branches should in this case be contained on a horizontal line.

The angle alpha of the frame can be determined by image processing, allowing by rotating the image by image processing repositioning the frame so as to have the angle alpha close to 0.

The method of the invention may further comprise a position determining step S4. During the position determining step S4, the distance and the relative orientation of the image acquisition module of the portable electronic device and the optical equipment are determined.

According to an embodiment of the invention, the distance and relative orientation of the image acquisition module of the portable electronic device and the optical equipment are determined using at least measuring means of the portable electronic device.

Indeed, the portable electronic may be equipped with measuring means such a stereo or 3D camera, telemeter that may be used to determine the distance and orientation of the optical equipment and/or the distant element.

According to an embodiment of the invention, the distance and relative orientation of the image acquisition module of the portable electronic device and the optical equipment are determined using at least measuring means including a printed sheet having specific printed features.

Typically, the pattern comprises at least one element of known dimension, such as a standard sheet having a standard dimension grid printed.

During the permanent marking detection step S4, at least one of the permanent markings on the optical equipment is detected using the image acquired by the image acquisition module of the portable electronic device in the second position.

When acquiring the picture of the pattern through the optical lens, the acquisition module is configured to have the focus on the spectacle frame. The spectacle frame being offset with respect to the pattern of at least several centimeters, preferably between 10 cm and 30 cm.

During the acquisition one may acquire a plurality of images and select those with the best contrast to limit shaking effects due to the fact that the user simultaneously holds the frame and the mobile device.

Alternatively, the acquisition may be triggered only when the mobile device is stable, for example using the accelerometer of the mobile device.

The image acquired show the permanent markings such as the micro engravings.

Detection of the permanent markings can be done for example by using a high-pass filtering (derived filter, Laplacian filter . . . ), which allows only the high spatial frequencies or by a contour detection for example using the Canny Deriche method.

The detection of the shape of the spectacle frame may be done using the same image processing method.

One may determine the shape of the right and left side of the spectacle frame, the position of the nose pads, the position and shape of the bridge.

As illustrated on FIG. 1, the method may further comprise prior to the parameter determining step S6 a scaling step S5.

During the scaling step S5, the scale of the image of the optical equipment is determined based on the standard distance of two permanent alignment markings on the same optical lens and/or by using a known size element positioned in the average plane of the optical equipment.

The known size element may be a complementary element such as a credit card or coin, or an element of the spectacle frame itself.

For example, a credit card or a known coin may be positioned next to the optical equipment and the distant element to provide a reference element used to determine the distances and relative orientations.

During the parameter determining step S6 at least one parameter of the optical equipment is determined based on the detected the permanent marking.

According to an embodiment of the invention, the least one parameter of the optical equipment is selected in the list consisting of the pupillary distance, the half-pupillary distance, height parameters, the far distance centering point, the addition of the progressive lens, the lens manufacturer.

For example, using an image processing, one may extract from the acquired image the position of the permanent marking.

According to a preferred embodiment, during the parameter determining step the position of the distance visual point relative to a reference point of the spectacle frame is determined. For example, the reference point of the spectacle frame is a reference point of the nose pad of the spectacle frame.

Determining the position of the permanent markings relative to a reference point of the spectacle frame may allow to determine the position of the ophthalmic lens in the spectacle frame, the optical function of the ophthalmic lens, for example the dioptric function, the optical design, the optical power or addition of the ophthalmic lens.

The dioptric function corresponds to the optical lens power (mean power, astigmatism etc . . . ) as a function of the gaze direction.

The wording "optical design" is a widely used wording known from the man skilled in the art in ophthalmic domain to designate the set of parameters allowing to define a dioptric function of an ophthalmic lens; each ophthalmic lens designer has its own designs, particularly for progressive ophthalmic lenses.

As for an example, a progressive ophthalmic lens "design" results of an optimization of a progressive surface so as to restore a presbyope's ability to see clearly at all distances but also to optimally respect all physiological visual functions such as foveal vision, extra-foveal vision, binocular vision and to minimize unwanted astigmatisms.

For example, a progressive lens design comprises:
a power profile along the main gaze directions (meridian line) used by the lens wearer during day life activities, distributions of powers (mean power, astigmatism, . . . ) on the sides of the lens, that is to say away from the main gaze direction.

These optical characteristics are part of the "designs" defined and calculated by ophthalmic lens designers and that are provided with the progressive lenses.

The optical function and/or dioptric function may be identified by the permanent markings on the ophthalmic lens.

Advantageously, by detecting and processing the permanent marking one may identify the optical function or at least the dioptric function of the optical lens a person is currently using so as to easily allow the person to order a new pair of spectacles having a similar, for example the same, optical function or dioptric function.

In most cases the identified features of the optical function are reported in the new equipment. Some of the features of the optical function may be adapted based on further data, for example the addition may be adapted based on the age of the wearer.

As indicated previously, based on the identified of the permanent markings it is possible to determine some features of the optical equipment.

For example, the permanent markings may be used to determine the fitting cross of the ophthalmic lens mounted in the spectacle frame.

Knowing the position of the micro engraving defined in the ISO standards for progressive ophthalmic lenses allows to determine the position of the fitting cross, generally located 4 mm above in the middle centering micro circles. The fitting cross may also be referenced with respect to the nose pads or to a particular point of nose pads that is known to be the point of contact with the nose of the wearer.

The scaling of the image may be done using the standard distance between the two micro circles, that is 34 mm.

In the case where one of the micro circles would not be visible, generally as nasal overflowed side, the scaling may be using a known size element as described previously.

Knowledge of the contact point on the nose pads with the nose may be very useful because it represents the reference point between the old and the new spectacles. One can take a second image of the wearer with the spectacles and estimate the portion of the nose pad in contact with the nose. One can also make a simple assumption that the nose pads of the current and new spectacle are positioned in the same manner and therefore not consider the reference point linked to the nose pads.

Once the position of the fitting cross relative to a reference point of the pads of the frame is known, the data may be used to determine features of the new spectacle to be provided to the wearer. For instance, measuring the vertical distance between the fitting cross and the nose pads position, it is possible for when ordering a new frame and new lens to fit the new lens on the new frame so that the vertical distance between the nose pads of the new frame and the fitting cross of the new lens is similar to the measured distance. As a consequence, the position of the fitting cross of the new lens according to the wearer eyes will be the same. If nose pads of the new frame show difference according to the frame, this vertical distance may be modified. For instance, if the nose pad width on the new frame is larger than the nose pad with of the frame, it is recommended to increase this verticale distance on the new eyewear, because the contact between the nose pad of the new frame and the nose of the user will be at a lower position.

The first point is to determine the contact point between the nose pads of the new spectacle and the nose of the wearer.

It is possible to use an image of the face of the wearer and make a virtual try to estimate the contact points and then use a simple rule.

It is possible to manage the differences spacing between the nose pads based on an average angle to the root of the nose or from the image.

Based on such data, the fitting cross may be positioned in the new spectacle frame.

The fitting cross may be positioned in the new spectacle frame so as to correspond to the primary gazing direction.

Advantageously, this allows ensuring optimal mounting of the progressive surface of the ophthalmic lens in the new spectacle frame.

Furthermore, the projection of the fitting cross in the shape of the frame of the new spectacle frame allows to define the mounting height and thus to propose an optical design compatible with the shape of the new spectacle frame.

The position of the micro circles may be used to determine precisely the interpupillary distance of the wearer. For example, one may determine the distance between the middle of the micro circles for the right and left lenses.

It is also possible to determine the left and right half interpupillary distance by determining the distance between firstly the middle of the micro circles and the middle of the bridge of the spectacle frame.

The interpupillary distance may be used to determine the features of the new spectacles.

It is possible, for example using an optical character recognition method on the markings, to determine the addition of the progressive lens.

Similarly, the position of the micro circles gives the position of the far vision point in the optical lens, generally located 8 mm above the middle of micro circles. It is then possible to make a measurement of the optical power at the far vision point using a portable electronic device.

The markings can be used to identify the type of optical design of the current equipment of the wearer. For example, some markings may provide reference to the lens manufacturer allowing to order the same optical design from the same lens manufacturer or a similar design from a different lens manufacturer.

The invention also relates to a method for ordering a new optical equipment for a user of a first optical equipment.

Figure 6:
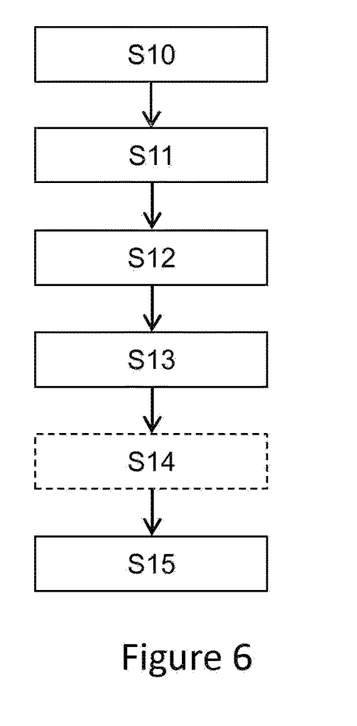
FIG. 6 is a flow chart representing an ordering method according to the invention.

As illustrated on FIG. 6, the ordering method of the invention may comprise:
- an optical equipment positioning step S10, during which the first optical equipment comprising a first pair of optical lenses mounted on a first spectacle frame is positioned in a first position,
- a portable electronic device positioning step11, during which a portable electronic device comprising an image acquisition module is positioned in a second position so as to acquire an image of a pattern seen through at least part of the optical lenses of the first optical equipment in the first position,
- an acquisition step S12, during which at least one image of the pattern seen through at least part of the optical lenses of the first optical equipment is acquired,
- a position adjustment step S13, during which the relative position of the portable electronic device and the first optical equipment is adjusted based on an identification of at least part of the optical equipment and/or the portable electronic device,
- an ordering step S15, during which an order request for a new optical equipment is sent to a distant entity, the order request comprising the at least one image acquired by the portable electronic device and new optical equipment identification data.

The ordering method of the invention may further comprise a parameter determining step S14, during which at least one optical parameter of the optical equipment is determined based on the image of the pattern seen through at least part of the optical lenses of the optical equipment in the first position.

Figure 7:
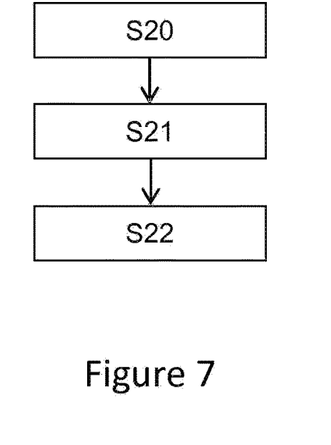
FIG. 7 is a flow chart representing an ordering method according to the invention.

As illustrated on FIG. 7, the invention further relates to a method for providing optical equipment for a person. The providing method comprises:
- an order receiving step S20 during which an order request generated by a method according to the invention and comprising at least an image of a pattern seen through at least part of the optical lenses of the first optical equipment of the person is received,
- a parameter determining step S21 during which at least one optical parameter of the optical equipment is determined based on the at least one received image,
- an optical equipment providing step S22 during which a new optical equipment is provided to the person based on the at least one optical parameter determined during the parameter determining step.

The invention has been described above with the aid of embodiments without limitation of the general inventive concept; in particular the mounted sensing device is not limited to a head mounted device.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for determining a parameter of an optical equipment including at least one optical lens including at least one permanent marking and being mounted in a spectacle frame, the method comprising:
   positioning optical equipment before a pattern in a first position;
   positioning a portable electronic device comprising an image acquisition module in a second position to acquire an image showing together the pattern seen through at least part of the at least one optical lens of the optical equipment in the first position and at least part of the spectacle frame of the optical equipment in the first position, the portable electronic device comprising a display, the pattern being generated by the display;
   detecting the at least one permanent marking on the at least one optical lens by using the image acquired by the image acquisition module of the portable electronic device in the second position; and
   determining at least one parameter of the optical equipment based on the position of the permanent marking,
   wherein the optical axis of the image acquisition module and the normal to the display going through the center of the display are parallel to one another but not coinciding so that the pattern goes through the at least one optical lens, is reflected on a mirror located substantially parallel to the plane of a front of the at least one optical lens, goes through the at least one optical lens again and is then detected by the image acquisition module of the portable electronic device.

2. The method according to claim 1, further comprising, prior to determining the parameter, determining a scale of the image of the optical equipment based on standard one or more of: (i) a standard distance of two permanent alignment markings on the same optical lens, and (ii) using a known size element positioned in the average plane of the optical equipment.

3. The method according to claim 2, wherein the at least one parameter of the optical equipment is selected from the list consisting of the pupillary distance, the half-pupillary distance, height parameters, the far distance centering point, the addition of the progressive lens, and the lens manufacturer.

4. The method according to claim 2, wherein, during the determining the at least one parameter, determining the position of the distance visual point relative to a reference point of the spectacle frame.

5. The method according to claim 2, wherein the position of the far vision reference point of the optical lens is determined during the determining the at least one parameter.

6. The method according to claim 1, wherein the at least one parameter of the optical equipment is selected from the list consisting of the pupillary distance, the half-pupillary distance, height parameters, the far distance centering point, the addition of the progressive lens, and the lens manufacturer.

7. The method according to claim 6, wherein, during the determining the at least one parameter, determining the position of the distance visual point relative to a reference point of the spectacle frame.

8. The method according to claim 6, wherein the position of the far vision reference point of the optical lens is determined during the determining the at least one parameter.

9. The method according to claim 1, wherein, during the determining the at least one parameter, determining the position of the distance visual point relative to a reference point of the spectacle frame.

10. The method according to claim 9, wherein the reference point of the spectacle frame is a reference point of a nose pad of the spectacle frame.

11. The method according to claim 1, wherein the position of the far vision reference point of the optical lens is determined during the determining the at least one parameter.

12. The method according to claim 11, wherein, during the determining the at least one parameter, determining at least one optical parameter of the at least one optical lens based on the image of a distant element seen through at least part of the at least one optical lens of the optical equipment in the first position.

13. The method according to claim 1, further comprising determining a distance and a relative orientation between the image acquisition module and the optical equipment.

14. The method according to claim 13, wherein the distance and the relative orientation between the image acquisition module and the optical equipment are determined using at least one measuring device of the portable electronic device.

15. The method according to claim 13, wherein the distance and the relative orientation of the image acquisition module of the portable electronic device and the optical equipment are determined using a printed sheet having specific printed features.

16. The method according to claim 1, wherein the at least one optical lens comprises two optical lenses mounted in the spectacle frame, and the method further comprises determining the interpupillary distance of a user, for which the optical equipment is intended, based on the position of the permanent marking.

17. A method for ordering a new optical equipment for a user of a first optical equipment, the method comprising:
   determining at least one parameter of the first optical equipment of the user by the method according to claim 1; and
   sending an order request for a new optical equipment to a distant entity, the order request comprising the value of the at least one parameter and new optical equipment identification data.

18. A method for providing a new optical equipment for a user of a first optical equipment, the method comprising:
   receiving the order request generated by the method according to claim 17;
   determining at least one parameter of the new optical equipment of the user based on the value of the determined at least one parameter of the first optical equipment; and
   providing the new optical equipment to the user based on the value of the determined at least one parameter of the new optical equipment.

19. The method according to claim 18, wherein during the determining the new optical equipment parameter, at least one parameter of the new optical equipment of the user is determined as substantially the same as the at least one determined parameter of the first optical equipment.

20. The method according to claim 1, wherein the portable electronic device is equipped with a measuring device configured to be used to determine a distance and an orientation of one or more of: (i) the optical equipment and (ii) a distant element.

* * * * *